United States Patent [19]

Heil et al.

[11] 4,330,279

[45] May 18, 1982

[54] FLUID SPRAY SYSTEM FOR DENTAL HANDPIECE

[75] Inventors: Donald J. Heil, Lake Villa; Thomas W. Albert, Bartlett, both of Ill.

[73] Assignee: American Hospital Supply Corporation, Evanston, Ill.

[21] Appl. No.: 109,761

[22] Filed: Jan. 7, 1980

[51] Int. Cl.³ .............................................. A61C 1/12
[52] U.S. Cl. ...................................... 433/82; 433/126
[58] Field of Search ....................... 433/82, 84, 85, 87, 433/126; 173/74

[56] References Cited

U.S. PATENT DOCUMENTS

| | | | |
|---|---|---|---|
| 1,039,728 | 10/1912 | Gilmore | 433/87 |
| 2,369,880 | 2/1945 | Bailenson | 433/127 |
| 2,685,737 | 8/1954 | Leff | 433/87 |
| 2,855,672 | 10/1958 | Franwick et al. | 433/84 |
| 3,061,930 | 11/1962 | Borden | 433/127 |
| 3,175,293 | 3/1965 | Borden | 433/127 |
| 3,199,196 | 8/1965 | Lieb et al. | 433/87 |
| 3,256,603 | 6/1966 | White | 433/127 |
| 3,256,604 | 6/1966 | Borden | 433/82 |
| 3,815,241 | 6/1974 | Lingenhohle et al. | 433/82 |
| 3,952,416 | 4/1976 | Lingenhöle | 433/82 |

FOREIGN PATENT DOCUMENTS 1270736 6/1968 Fed. Rep. of Germany ........ 433/82

Primary Examiner—Gene Mancene
Assistant Examiner—John J. Wilson
Attorney, Agent, or Firm—Tilton, Fallon, Lungmus

[57] ABSTRACT

A dental handpiece having an improved water/air spray system including a pair of substantially parallel tubes, one for water and the other for chip air, extending through the handle of the handpiece and terminating in a nozzle chamber of oval cross section. The tubes are generally cylindrical but are partially deformed at their distal ends, such deformation constituting a flattening of adjacent wall portions of the respective tubes. Such adjacent wall portions are disposed in contiguous relation and are cut away for a limited distance at the discharge end of the tube assembly to define the unitary nozzle chamber. The chamber has an oval discharge orifice for directing an elliptical spray pattern towards the tip of the dental bur. At the opposite end of the handpiece, the handle is equipped with a plug terminating in an external end face. Tubular extensions project from that end face for conveying air to the drive air and chip air passages. An open channel formed in the end face of the plug communicates with annular recesses disposed about such extensions, and each extension is provided with a lateral aperture communicating with the surrounding recess. The open side of the channel and the ends of the recesses are sealed by a sealing member when the handpiece is in operation.

21 Claims, 12 Drawing Figures

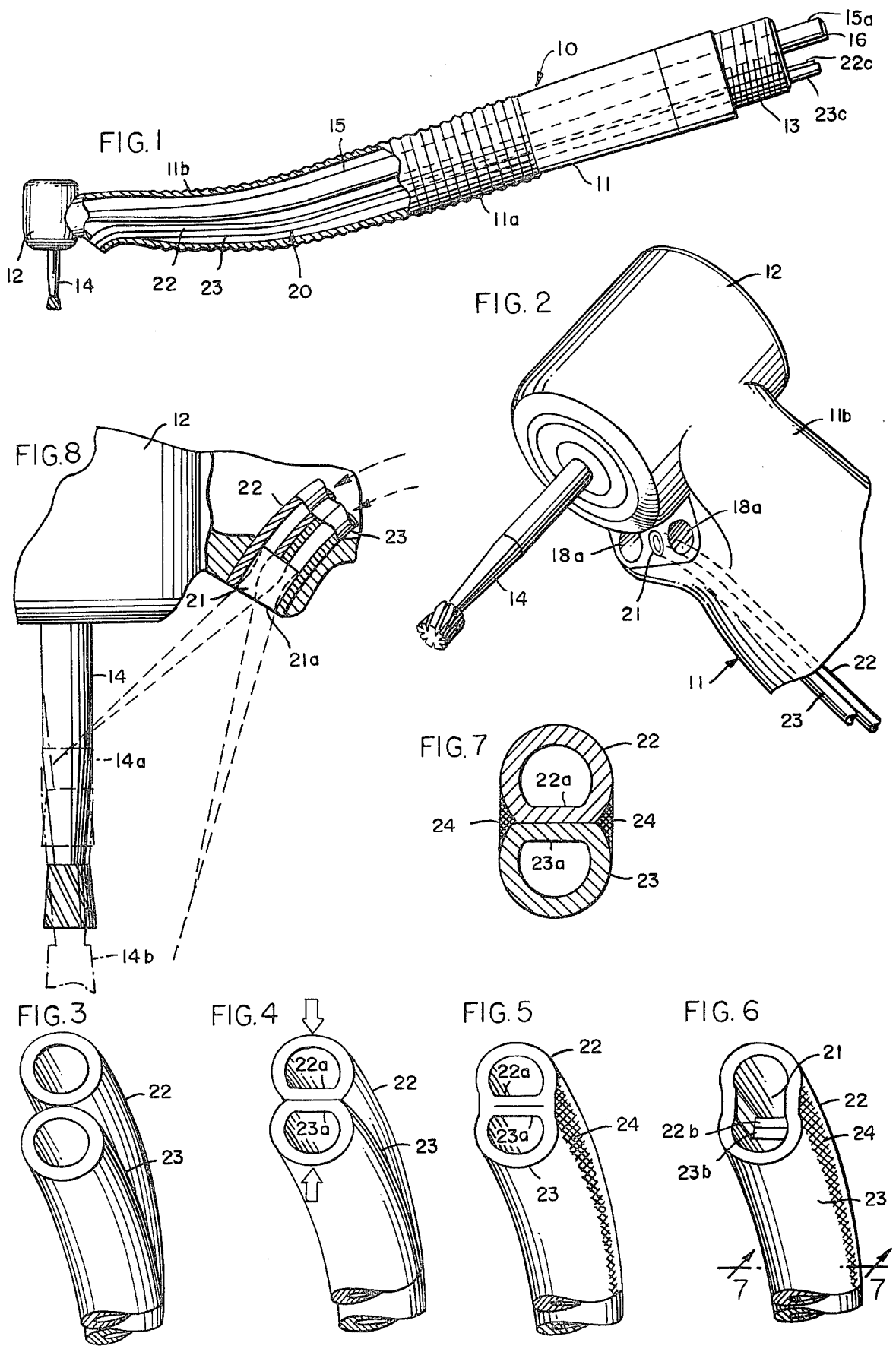

FLUID SPRAY SYSTEM FOR DENTAL HANDPIECE

BACKGROUND

High speed dental handpieces are commonly provided with nozzles for directing air and water in spray form towards the tips of the dental burs. The water/air spray performs the dual functions of cooling the work area and clearing debris from that area. To be effective for those purposes, the spray should be focused on the cutting area. Achieving that objective presents difficulties because burs are available in different lengths and configurations. In general, the shanks of such burs have lengths ranging between short, standard, and long, and the cutting tips of such burs vary widely in length, diameter, and configuration. If a dental handpiece has a wide-angle spray pattern to encompass all of the common bur sizes, only a small proportion of the cooling water will actually be directed towards the tip of any given bur, thereby providing a low level of cooling effectiveness for the amount of water discharged. To avoid flooding areas remote from the bur tip with water which performs no useful cooling function, a narrow-angle spray pattern might be provided; however, in that case, the spray may be too narrow to be useful with burs of different length.

The intermixing of water and air to form the aerosol spray may occur either internally or externally of the handpiece. U.S. Pat. No. 3,952,416 shows an internal mixing system in which a portion of the drive air is diverted and mixed with water in a chamber within the neck of the handpiece, the mixture then being discharged through a passage in the head of that handpiece. Other patents disclosing remote or internal mixing are U.S. Pat. Nos. 3,256,603 and 3,175,293. External mixing is typically provided, at least in one commercial line of handpieces, by concentric water and chip air tubes which have their discharge ends disposed immediately adjacent the heads of such handpieces. Simultaneous discharge of air and water from the pressurized lines causes an aerosol spray to be directed towards the dental bur driven by such a handpiece.

The pressure of the water available to form the spray is typically about 10 psi; hence, it is the air under substantially greater pressure that is responsible for propelling the droplets so that they may perform their cooling and clearing functions more effectively. Greater air pressures of approximately 60 psi are available in those systems which provide chip air lines and, consequently, chip air provides an ideal vehicle for the water particles in the development of an aerosol spray. In those systems which do not provide chip air lines, a small amount of drive air at typical pressures of about 30 psi may be bled off to develop the aerosol spray.

While it is advantageous to design a dental handpiece so that it may utilize chip air, if available, in forming the water/air spray and, if not available, will automatically use drive air for that purpose, such a handpiece has in the past been relatively complex and expensive. One such construction involves the interposition of a manifold chamber along the drive air line within the handle of the handpiece. A bleed port extends between the drive air passage and the manifold chamber and flow therethrough is controlled by a poppet valve which is normally closed by the greater pressure of chip air supplied to the manifold chamber by a separate chip air line. Another line leads from the manifold chamber to the spray nozzle. If chip air is available, then the poppet valve is automatically closed and such air flows through the manifold chamber to the spray nozzle, whereas if no chip air is available the valve automatically opens and allows a limited flow of drive air to bleed through the chamber to the nozzle.

Other patents indicating the state of the art are U.S. Pat. Nos. 2,855,672, 2,369,880, and 3,061,930.

SUMMARY

A main object of this invention is to provide a high speed dental handpiece having a spray system which eliminates, or at least greatly reduces, the problems and difficulties described above. More specifically, this invention is directed to a handpiece having an improved air/water spray system which directs a cooling and clearing aerosol spray towards the work area even when burs of a wide range of lengths are utilized, without at the same time directing excessive amounts of water towards adjacent areas where cooling is not required, and which forms such a spray whether the air is derived from a chip air line or from a drive air line. While the system may be used with handpieces of different size, its functional effectiveness and structural simplicity makes it particularly suitable for miniaturized turbine-driven handpieces.

The handpiece is provided with a single nozzle chamber for receiving water and air (either chip air or drive air) from lines which extend through the handle of the handpiece. The chamber and its outlet are oval in cross sectional configuration with the long axis of the oval lying in the same plane as the rotational axis of the bur and with the nozzle opening being directed towards the tip of a mounted bur of standard length. Consequently, the oval spray pattern, elongated in a direction along the bur axis but confined in directions lateral to that axis, provides effective cooling and clearing actions for burs of shorter and longer shank length, as well as for burs of standard shank length, without the undesirable discharge of excessive volumes of water. In addition, the nozzle chamber serves as a pre-convergence chamber which effectively increases the distance between the separate outlets of the water and chip air tubes and thereby insures proper air/water intermixing even for handpieces of smaller or miniature dimensions.

The air and water tubes leading to the nozzle chamber extend through the handle of the handpiece in generally parallel side-by-side relation. The nozzle chamber is formed by removing or cutting away contiguous wall portions from such tubes at the extreme distal ends thereof. Although such tubes are cylindrical for the most part, the contiguous wall portions approaching the discharge end of the tube assembly are flattened and such tubes are secured together with such flattened wall portions in direct contact with each other. The result is that the nozzle chamber, formed by removal of such flattened contiguous wall portions at the distal end of the spray tube assembly, is generally oval in cross sectional configuration.

The air tube leading to the discharge chamber is referred to herein as a chip air tube, as distinguished from the drive air supply tube which also extends through the handle of the handpiece. Both the chip air tube and the water supply tube have portions which project beyond the end plug at the proximal end of the handpiece. Similarly, an extension tube or sleeve for drive air projects beyond the planar end face of the plug. An annular recess is provided in the end plug about each extension for chip and drive air, and a transverse groove or channel is formed in the end plug between such recesses. The tubular extensions or sleeves are provided with apertures which communicate directly with the recesses, and a sealing member seals the open side of the channel, as well as the open ends of the annular recesses, when the handpiece is coupled to a supply hose. As a result, the transverse passage defined by the channel communicates only with the chip air and drive air lines. If the handpiece hose is coupled to a dental console which supplies chip air at relatively high pressures (generally about 60 psi), then such air is utilized by the spray assembly of the handpiece to produce the air/water spray as needed. A limited amount of such air also bleeds through the transverse passage or channel into the drive air line but is insufficient to produce any significant effect on turbine operation. On the other hand, should the handpiece hose be connected to a dental unit that provides only drive air and water, and supplies no chip air, then the flow of air through the transverse channel is reversed with a limited amount of drive air being bled into the chip air line of the handpiece to be used in producing the aerosol spray. Again, because of the small size of the aperture or orifice interposed between the drive air and chip air passages of the handpiece, the bleeding of such limited amounts of drive air for aerosol spray formation has no appreciable effect on turbine operation.

Other objects, features, and advantages of the invention will become apparent from the drawings and specification.

DRAWINGS

FIG. 1 is a side elevational view, partly in section, of a dental handpiece embodying this invention.

FIG. 2 is a perspective view of the head and neck portions of such handpieces.

FIGS. 3–6 are a series of fragmentary perspective views illustrating the sequence of steps in the construction of the spray tube assembly at the fluid discharge end thereof.

FIG. 7 is a cross sectional view taken along line 7—7 of FIG. 6.

FIG. 8 is a fragmentary side elevational view, partly in section, showing the structural relationship and functioning of the spray tube assembly and its discharge chamber.

Figure 11:
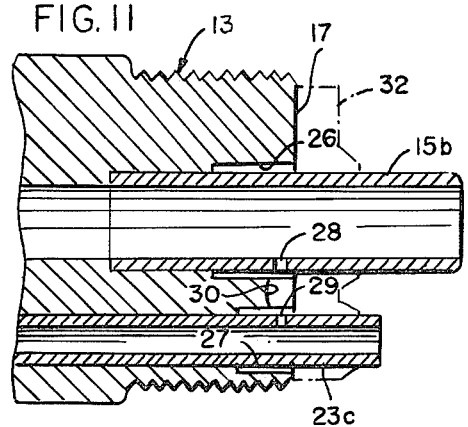
FIG. 11 is a longitudinal sectional view taken along line 11—11 of FIG. 10.

FIG.—12 is a sectional view similar to FIG. 11 but showing the parts in disassembled condition.

DETAILED DESCRIPTION

Referring to the drawings, the numeral 10 generally designates a contra-angle turbine-driven dental handpiece having an elongated hollow handle 11 terminating at its distal end in a head assembly 12 and at its proximal end in an end plug or connector 13. The plug is externally threaded so that the handpiece's proximal end may be coupled to a conventional hose leading to any of a variety of dental units or consoles which provide the pressurized sources of supply for air and water for handpiece operation. As shown, the main body portion 11a of the handle is straight and tapers gradually in a distal direction towards the angularly-oriented neck portion 11b leading to head assembly 12. An air-driven turbine (not shown) is mounted within the head assembly and includes a chuck for releasably supporting a conventional dental bur 14. A drive air tube extends through the handle to supply air under pressure for driving the turbine. For ease of assembly, the drive air tube may be formed in sections with one section 15a leading from the head assembly 12 to the end plug 13 and another section 15b projecting proximally from the plug. Exhaust air is discharged from the turbine into the hollow handle and passes from the handle into the hose through a tubular extension 16 of plug 13 which, in the illustration given, is formed integrally with that plug. The drive air extension or section 15b and the exhaust air extension 16 provide connections for direct communication to the drive air and exhaust air conduits of the hose (not shown).

Figure 9:
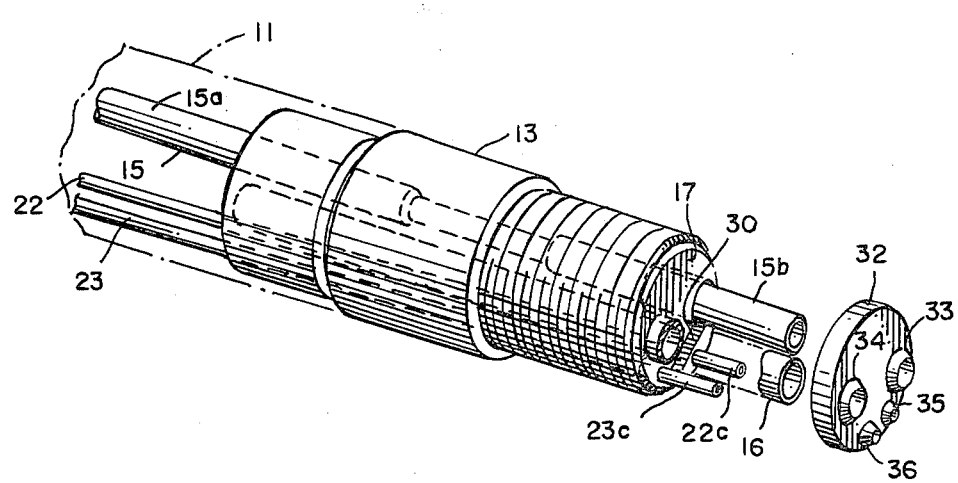
FIG. 9 is a perspective view of the proximal end of the handpiece with its sealing gasket removed and with the exhaust air tube broken away to illustrate details of construction.
Figure 10:
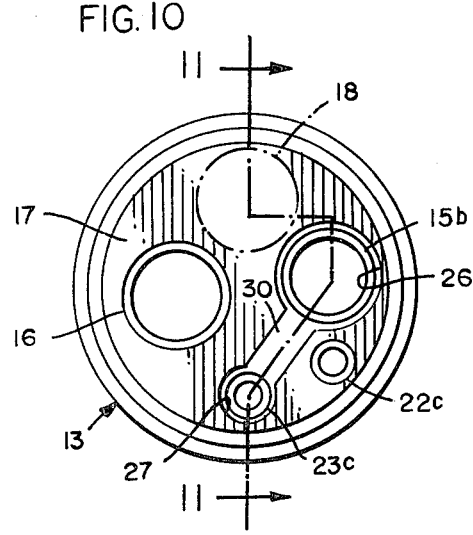
FIG. 10 is an enlarged view of the proximal end of the handpiece with the sealing gasket removed.

If desired, a light-transmitting waveguide, typically in the form of a sheathed glass fiber bundle, may extend through the handpiece handle for illuminating the work area. Such a waveguide forms no direct part of this invention and is therefore depicted in phantom at 18 in FIG. 10. The significance of the waveguide in relation to this invention lies primarily in demonstrating that space within the handle of the handpiece is at a premium because of the various conduits which must pass through it, and in the further fact that there is only limited available space for the spray tube assembly 20 and its nozzle chamber 21 to be described in detail hereinafter. FIG. 2 reveals that where fiberoptic illumination is provided, the light bundle may be bifurcated near the head of the handpiece to provide a pair of spaced light-emitting end surfaces 18a. Such arrangement is helpful in reducing shadows in the work area at the tip of bur 14 but it also restricts the available space for fluid discharge chamber 21, especially where the handpiece is of the miniaturized type as shown.

The spray tube assembly 20 consists primarily of a pair of small-bore tubes 22 and 23 which extend through plug 13 and through handle 11 to a discharge point adjacent head assembly 12. Tubes 22 and 23 are water and chip air tubes, respectively, for delivering water and air to produce a cooling and debris-clearing aerosol spray at the head end of the handpiece (FIG. 8). The term "chip air" is used to indicate that in the preferred operation of the handpiece tube 23 would normally carry air at pressures of approximately 60 psi, well above the pressure of drive air (typically about 30 psi) carried by drive air tube 15. Depending on the controls used and the dental unit to which handpiece 10 is connected, chip air tube 23 may be used separately to discharge a jet of dry air for dislodging chips or cutting debris from the work area. For purposes of this invention, such independent use of tube 23 bears no particular significance; however, to help in distinguishing tube 23 from other air transmitting tubes, and because even when used in conjunction with water tube 22 to produce an aerosol spray the chip air tube 23 does indeed function to move cutting debris from the work area, the term "chip air" will be used extensively herein in referring to tube 23.

At the distal end of the handpiece, the two tubes 22 and 23 are secured together by solder, welding, or other suitable adhesive or bonding agent. Preferably, the attachment commences along that section of the tube assembly which extends through the neck portion 11b of the handle and continues distally to the ends of the tubes.

Throughout most of their length, tubes 22 and 23 are cylindrical in configuration. However, as they approach the head end of the handpiece, the adjacent wall portions 22a and 23a are flattened as depicted in FIG. 7. The planar opposing wall portions 22a and 23a are disposed in contiguous relation and are fixed in that relation by solder (or other bonding agent) 24. The result is that the passages of the respective tubes are reduced slightly in cross section in the area of deformation and interconnection; however, such deformation also substantially reduces the combined outside dimensions of the two tubes when measured along a line passing through the axes of both.

Such deformation and unification also gives rise to a simple and highly effective way of forming a fluid discharge nozzle 21 of generally oval cross section at the distal end of the spray tube assembly. FIGS. 3–6 represent in somewhat schematic fashion the succession of fabrication steps. The two tubes 22 and 23 are first arranged with their distal ends in juxtaposition as shown in FIG. 3. Compressive force is then applied to reduce the combined cross sectional dimension of the paired tubes and to deform the contacting walls 22a and 23a so that they assume the planar configurations depicted in FIG. 4. The deformed tubes are then fixed together in their positions of mutual engagement by suitable bonding means represented in FIGS. 5 and 7 by solder 24. Thereafter, the common wall portions which separate the passages of the respective tubes at the distal end of the assembly are cut away to 22b and 23b to define unified oval-shaped nozzle chamber 21 (FIG. 6).

After the spray tube assembly 20 has been mounted within the hollow handle of the handpiece, the parts assume the orientation most clearly illustrated in FIG. 8. The nozzle chamber 21 has its discharge orifice 21a facing the work area at the cutting end of bur 14. The perimeter of the orifice lies along a plane normal to the direction of discharge, and the nozzle is oriented so that the greater transverse axis of its orifice 21a, and the greater transverse axis of the oval-shaped nozzle chamber (when viewed in cross section), lie in a plane extending along the rotational axis of the rotor assembly and the bur 14 supported by it. Consequently, the angle of spread of the spray pattern is far greater in a plane extending along the axis of the bur (vertically, as shown in FIG. 8) than in directions normal to that plane. The result is that the cooling and chip-clearing air/water spray will be properly directed towards the work area, and specifically towards the tip of the bur, regardless of whether the bur is of standard length, as depicted in full lines in FIG. 8, or has a shorter or longer shank as indicated by lines 14a and 14b, respectively. Of particular significance is the fact that such coverage and density of flow towards the work area requiring cooling and clearing may be achieved without discharging excessive and ineffective volumes of water into the patient's mouth. The oval spray pattern developed by the nozzle concentrates the spray in the area requiring cooling and chip removal.

The depth or axial dimension of chamber 21 will vary depending on the cross sectional dimensions of the passages defined by tubes 22 and 23 and by other factors such as the fluid pressures involved. In a system in which the inside diameters of such tubes adjacent the head of the handpiece are approximately 0.02 inches, resulting in a nozzle chamber having an oval cross sectional configuration measuring approximately 0.02 by 0.04 inches in its transverse dimensions, a chamber depth or axial dimension of approximately 0.06 inches has been found particularly effective. It is to be understood, however, that these dimensions and proportions are given only for illustrative purposes and that considerable variation is permissible. In general, the depth or axial dimension of chamber 21 must not be so great that the back pressure created by the chamber exceeds the supply pressure of either the water or the air delivered by tubes 22 and 23, respectively.

Figure 12:
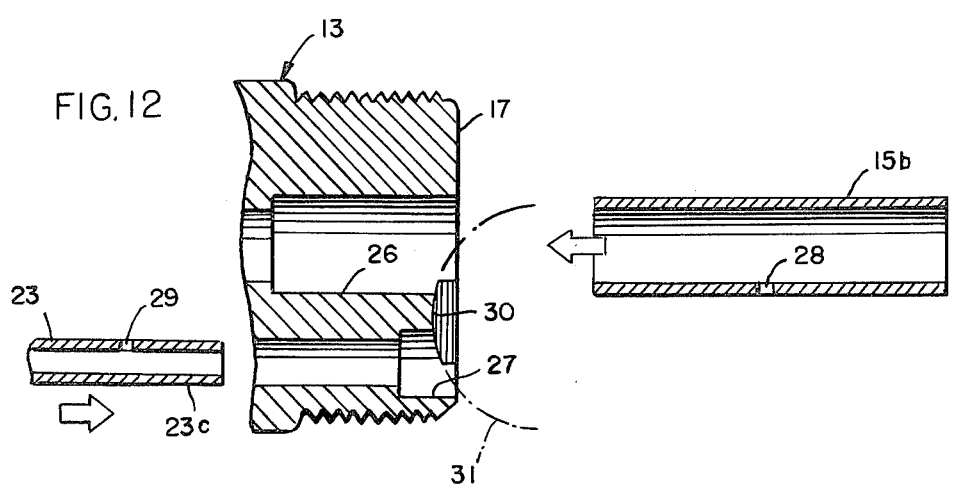

The water and air tubes 22 and 23 extend through the handle of the handpiece and through proximal end plug 13, terminating in end portions 22c and 23c which project beyond the plug's planar end face 17. Similarly, the tubular extension 15b of the drive air passage 15 projects from the end face of the plug. The plug is bored to receive the water and chip air supply tubes as well as the drive air extension tube, and as shown most clearly in FIGS. 11 and 12, is counterbored to define annular recesses 26 and 27 about the drive air extension tube 15b and chip air tube portion 23c immediately adjacent end face 17. When the parts are assembled as shown in FIG. 11, lateral openings 28 and 29 in the side walls of drive air tube extension 15b and chip air tube portion 23c communicate with the annular recesses 26 and 27. A transverse groove or channel 30 formed in end face 17 extends between such recesses 26 and 27, the recesses therefore serving as manifold chambers for flow through the channel between openings 28 and 29. The channel may be formed in the end plug by any suitable means as, for example, by milling, cutting, casting, or molding. It is evident from FIG. 12 that a milling or cutting operation is particularly appropriate, the outline of the cutting tool being partially represented by phantom line 31.

The openings or apertures 28 and 29 may be formed by drilling, cutting, piercing, or any of a variety of known aperture-forming techniques. The size of at least one of the apertures, in this case aperture 29 in the end portion of chip air tube 23, is critical but depends on a number of variables including the size of the handpiece and its flow passages, the fluid pressure involved, and on factors such as the type of turbine utilized, the torque and speed requirements of the handpiece, etc. For a miniaturized contra-angle handpiece having an air turbine capable of operating at speeds between 300,000 to 500,000 rpm at drive air pressures of approximately 30 psi, and having a chip air line carrying air pressures of about 60 psi, with passage dimensions adjacent the head of the handpiece approximating those already indicated, an aperture having a diameter of approximately 0.03 inches has been found effective. Aperture 28 is larger (for the example just given, such aperture may be approximately 0.06 inches) so that the flow of air between the drive air passage and the chip air passage is controlled by aperture 29.

A disc-shaped sealing member or gasket 32 having openings 33–36 adapted to receive the tubular extensions for drive air, exhaust air, water, and chip air, respectively, fits over such extensions and sealingly engages the planar end face 17 of plug 13, thereby closing off the open side of transverse channel 30 as well as the ends of the annular recesses or manifold chambers 26 and 27. Ideally, the sealing member is formed of a resilient elastomeric material and is held in place either by adhesive attachment to end face 17 or by the axial force exerted by the hose coupling (not shown) when that coupling is threadedly connected to plug 13. It will be noted that the outer surface of sealing member 32 is provided with annular protrusions about openings 33-36 to promote fluid-tight sealing engagement with the tubular conduits of the hose to which the handpiece is to be connected.

The direction and source of the air flowing through transverse channel 30 will depend on the type of dental unit to which the proximal end of the flexible hose is connected. Preferably, such hose is connected to a unit having outlets for chip air, drive air, and water at typical pressures of about 60 psi, 30 psi, and 10 psi, respectively. In such a case, when the handpiece 10 is in use, chip air at relatively high pressure bleeds through orifice 29 into the drive air passage but the amount of air so directed is insufficient to have any appreciable effect on turbine operation. The major portion of the chip air flows axially through the chip air tube 23 to nozzle 21 and is intimately mixed with water discharged from tube 22 to form the air/water spray indicated in FIG. 8.

On the other hand, should the proximal end of the hose be connected to a dental unit that has no chip air supply line, but only supply lines for drive air and water, then air will bleed through transverse passage 30 in the opposite direction. Specifically, a small fraction of drive air will be diverted laterally through aperture 28, annular recess 26, channel 30, annular recess 27, and aperture 29 into the passage of chip air tube 23. Such air, transmitted to the nozzle 21 by the chip air tube 23, is thus available to form an air/water spray in the same manner already described.

The amount of air bleeding from the drive air passage into the chip air passage in insufficient to produce any adverse effect on turbine operation. Furthermore, although some of the air bleeding from the drive air passage into the chip air passage would necessarily flow in a reverse direction into the chip air conduit of the handpiece hose, such reverse flow does not adversely affect the formation of an effective aerosol spray adjacent the head of the handpiece. The water/air spray system as disclosed herein not only eliminates the need for a poppet or check valve between the drive air and chip air passages, but also eliminates the need for capping or plugging the proximal end of tube 23c should the handpiece hose be connected to a dental unit having no chip air supply line.

While in the foregoing we have disclosed an embodiment of the invention in considerable detail for purposes of illustration, it will be understood by those skilled in the art that many of these details may be varied without departing from the spirit and scope of the invention.

We claim:

1. A dental handpiece comprising a hollow handle having a proximal end portion adapted for connection to a supply hose containing conduits for the supply of air and water to said handle, an elongated body portion, and a neck portion terminating at its distal end in a head assembly; said head assembly including a housing, an air turbine within said housing adapted to be driven by air supplied through said handle, and a chuck for operatively connecting a dental bur to said turbine; wherein the improvement comprises said handle containing a spray tube assembly comprising a pair of tubes defining passages for conducting water and chip air from the proximal end of said handle to a nozzle adjacent said head assembly; said nozzle including a chamber of oval cross sectional configuration terminating in an oval discharge orifice facing towards the location for the tip of a dental bur when the same is supported by said head assembly; said nozzle having the greater transverse axes of its oval chamber and oval discharge orifice extending in the same plane as the rotational axis of said turbine, chuck, and bur.

2. The handpiece of claim 1 in which said chamber has a cross sectional configuration and size substantially the same as the outline of said discharge orifice.

3. The handpiece of claim 1 in which said tubes are disposed in substantially parallel relation and said orifice lies in a plane substantially normal to the direction of flow through said nozzle.

4. A dental handpiece comprising a hollow handle having a proximal end portion adapted for connection to a supply hose containing conduits for the supply of air and water to said handle, an elongated body portion, and a neck portion terminating at its distal end in a head assembly; said head assembly including a housing, an air turbine within said housing adapted to be driven by air supplied through said handle, and a chuck for operatively connecting a dental bur to said turbine; wherein the improvement comprises said handle containing a spray tube assembly comprising a pair of tubes defining passages for conducting water and chip air from the proximal end of said handle to a nozzle adjacent said head assembly; said nozzle including a chamber of oval cross sectional configuration terminating in an oval discharge orifice facing towards the location for the tip of a dental bur when the same is supported by said head assembly; said nozzle having the greater transverse axes of its oval chamber and oval discharge orifice extending in the same plane as the rotational axis of said turbine, chuck, and bur; a drive air tube extending through said handle for delivering drive air to said turbine; said handle being equipped with a connector plug at the proximal end thereof; said plug having an end face and having tubular extensions for said drive air, chip air, and water tubes projecting from said end face; said end face being provided with an annular recess extending about the extension for said drive air and chip air tubes and having a transverse channel extending between said recesses; said drive air and chip air tubes having lateral apertures therein communicating with said recesses and said channel.

5. The handpiece of claim 4 in which said channel and said recesses have open sides extending along said end face; said handpiece including a sealing member engaging said end face to seal said channel and recesses along the open sides thereof.

6. The handpiece of claim 5 in which said sealing member is resilient.

7. The handpiece of claim 4 in which one of said apertures is larger than the other.

8. The handpiece of claim 7 in which the smaller of said apertures is provided in the tubular extension for said chip air tube.

9. A dental handpiece comprising a hollow handle having a proximal end portion adapted for connection to a supply hose containing conduits for the supply of air and water to said handle, an elongated body portion, and a neck portion terminating at its distal end in a head assembly; said head assembly including a housing, an air turbine within said housing adapted to be driven by air supplied to said handle, and a chuck for operatively connecting a dental bur to said turbine; wherein the improvement comprises said handle containing a spray tube assembly comprising a pair of generally cylindrical tubes disposed in side-by-side relation and defining passages for conducting water and chip air from the proximal end of said handpiece to a nozzle disposed adjacent said head assembly; said spray tube assembly including a distal section along which said tubes are joined together with adjacent wall portions flattened and disposed in mutual engagement; said adjacent wall portions of said tubes being cut away at said distal section to define a unitary nozzle chamber having a discharge orifice for directing a spray of water and chip air towards the cutting end of a dental bur.

10. The handpiece of claim 9 in which said flattened adjacent wall portions of said tubes are disposed within the neck portion of said handle and extend to said nozzle chamber.

11. The handpiece of claim 10 in which the outline of said orifice and the cross section of said chamber are of generally oval configuration, the greater transverse axes of said oval chamber and oval orifice extending in a plane lying along the rotational axis of said turbine, chuck, and bur.

12. The handpiece of claim 11 in which the cross sectional dimensions of said chamber are substantially the same as said orifice.

13. The handpiece of claims 9, 10, 11, or 12 in which a drive air tube extends through said handle for delivering drive air to said turbine; said handle being equipped with a connector plug at the proximal end thereof; said plug having an end face and having tubular extensions for said drive air and chip air projecting from said end face; said end face having an annular recess extending about each of said extensions and having a transverse channel extending between and communicating with said recesses; said extensions having lateral apertures therein communicating directly with said recesses extending about the respective extensions.

14. The handpiece of claim 13 in which said channel and said recesses have open sides extending along said end face; said handpiece including a sealing member engaging said end face to seal said channel and recesses along the open sides thereof.

15. The handpiece of claim 13 in which one of said apertures is larger than the other.

16. The handpiece of claim 15 in which the smaller of said apertures is provided in the tubular extension for said chip air tube.

17. A dental handpiece comprising a hollow handle having a proximal end portion adapted for connection to a hose containing supply conduits for drive air, chip air, and water, an elongated body portion, and a neck portion terminating in a head housing containing an air-driven turbine; wherein the improvement comprises said handle containing a spray tube assembly comprising a pair of tubes arranged in side-by-side relation and defining passages for conducting water and chip air from the proximal end of said handle to a discharge point adjacent said head housing; a drive air tube extending through said handle for supplying drive air to said turbine; and a connector plug secured to said handle at the proximal end thereof for connecting said handpiece to a supply hose; said plug having an external end face and having extensions of said drive air tube and said chip air tube projecting therefrom; said end face having an annular recess extending about each of said extensions and having a transverse channel extending between said recesses; said extensions being provided with lateral apertures within said recesses communicating with said channel.

18. The handpiece of claim 17 in which said channel and recesses are open-sided along the face of said plug; said handpiece including a sealing member engaging said end face to seal said channel and recesses along the open sides thereof.

19. The handpiece of claim 18 in which said sealing member is resilient.

20. The handpiece of claim 17 in which one of said apertures is substantially larger than the other.

21. The handpiece of claim 20 in which said larger aperture is formed in the extension for said drive air tube.

* * * * *